United States Patent [19]

Creaven et al.

[11] Patent Number: 5,342,613
[45] Date of Patent: Aug. 30, 1994

[54] PHARMACEUTICAL COMPOSITIONS AND USE THEREOF IN THE TREATMENT OF PSORIASIS

[75] Inventors: Patrick J. Creaven, Eggertsville, N.Y.; Kazuyoshi Hori, Fuji; Hiroshi Ishimaru, Tokyo, both of Japan

[73] Assignee: Health Research Inc., Buffalo, N.Y.

[21] Appl. No.: 958,595

[22] Filed: Oct. 8, 1992

Related U.S. Application Data

[63] Continuation of Ser. No. 704,686, May 17, 1991, abandoned, which is a continuation of Ser. No. 290,497, Dec. 27, 1988, abandoned.

[51] Int. Cl.$^5$ .............................. A61K 37/02
[52] U.S. Cl. .................. 424/85.1; 424/85.2; 424/85.4; 514/2; 514/12
[58] Field of Search ............. 424/85.1, 85.2, 85.4; 514/2, 12

[56] References Cited

U.S. PATENT DOCUMENTS

| | | | |
|---|---|---|---|
| 4,822,605 | 4/1989 | Powell | 424/85.2 |
| 4,929,442 | 5/1990 | Powell | 424/85.2 |
| 4,978,332 | 12/1990 | Luck et al. | 514/430 |

FOREIGN PATENT DOCUMENTS

| | | | |
|---|---|---|---|
| 0158286 | 10/1985 | European Pat. Off. | C12N 15/00 |
| 0325471 | 1/1989 | European Pat. Off. | A61K 37/36 |

OTHER PUBLICATIONS

Griffiths, C. E. M., J. Am. Acad. Dermatol. 27(1) 1992 pp. 98–101.
Iverson, O. J. J. Investigative Dermatol. 85(5) 1990, pp. 41S–43S.
Krueger et al J. Invest. Dermatol. 95(5) 1990 pp. 56S–58S.
Griffiths, C. E. M. et al, Springer Seminars in Immunopathology, vol. 13, No. 314 1992 pp. 441–454.
Karasek, M. A. Cutis 46(4) 1990, pp. 307–310.
Patent Abstracts of Japan, vol. 12, No. 186 (C-500) [3033] Field C (May 31, 1988).
European Search Report for EP 89122317 (Jul. 19, 1991).

Primary Examiner—Christine M. Nucker
Assistant Examiner—Chris Dubrule
Attorney, Agent, or Firm—Pennie & Edmonds

[57] ABSTRACT

A pharmaceuticl composition and a method for its use in the treatment of psoriasis are provided wherein the composition comprises tumor necrosis factor as an active ingredient and at least one pharmaceutically acceptable carrier, diluent or excipient.

3 Claims, No Drawings

PHARMACEUTICAL COMPOSITIONS AND USE THEREOF IN THE TREATMENT OF PSORIASIS

This is a continuation of application Ser. No. 07/704,686, filed May 17, 1991, now abandoned, which is a continuation of application Ser. No. 07/290,497, filed Dec. 27, 1988, now abandoned.

TABLE OF CONTENTS

|    |                                      | Page |
|----|--------------------------------------|------|
| 1. | Background Of The Invention          | 2    |
|    | 1.1. Technical Field                 | 2    |
|    | 1.2. Background Art                  | 3    |
| 2. | Summary Of The Invention             | 8    |
| 3. | Description Of Preferred Embodiments | 15   |
|    | 3.1. Reference Example               | 15   |
|    | 3.2. Example 1                       | 18   |
|    | 3.3. Example 2                       | 19   |
|    | 3.4. Example 3                       | 19   |
| 4. | Claims                               | 20   |
| 5. | Abstract Of The Disclosure           | 22   |
| 6. | Declaration And Power Of Attorney    | 23   |

1. BACKGROUND OF THE INVENTION

1.1. Technical Field

The present invention relates to pharmaceutical compositions for use in the treatment of psoriasis. More particularly, it relates to pharmaceutical compositions containing tumor necrosis factor or "TNF" as an active ingredient for treating psoriasis in humans. The invention also relates to a method for treating psoriasis by administering TNF in effective anti-psoriatic amounts to patients suffering from the disease.

1.2. Background Art

Psoriasis is a chronic skin disease long recognized for its peculiar clinical symptoms characterized by circumscribed red patches covered with white scales, and often accompanied by varying degrees of discomfort. It has been determined that the disease is not contagious; however, its cause and mechanism have not yet been elucidated. See, Kruger, G. G., "Psoriasis: Current Concepts of its Etiology and Pathogenesis", The Year Book of Dermatology (1981), edited by Dobson, R. L. and Thiers, B. H. Due to the characteristic formation of skin lesions and eruptions, psoriasis gives its victims an unfavorable psychological outlook on life. Among people in Western countries, about 2% of the total population suffer from the disease.

Psoriasis is considered to be a pluricausal hereditary disease whose onset occurs due to the genetic makeup in the body, and which is stimulated by the action of various other factors, such as infection, drugs, food, climate and stress, any or all of which can trigger the genetic cause. Since it is known that psoriasis has a close relationship with a histocompatibility antigen (HLA) which exhibits polymorphism due to the variation of the HLA gene, it is clear that psoriasis is a hereditary disease.

The occurrence of psoriasic lesions and their remission are often alternately experienced over several years. There are two characteristic symptoms of psoriasis, namely, an inflammatory response common to that caused by other superficial skin diseases and a tendency toward abnormal growth of cuticle. Many researchers have sought to elucidate the mechanism of the inflammatory response from the immunological viewpoint and the mechanism of the tendency to abnormal growth of cuticle from the cell physiological viewpoint. However, these mechanisms have not yet been successfully elucidated. See, Beutner, E. H., "Autoimmunity in Psoriasis" (CRC Press, Boca Raton, 1982).

Psoriasis is representative of those diseases accompanied by an inflammatory cornification of the skin, and the number of patients suffering from psoriasis is increasing. Various classifications have been proposed for psoriasis, but it is generally classified into psoriasis vulgaris, pustular psoriasis, psoriatic arthritis, guttate psoriasis, and the like. Of these, psoriasis vulgaris is the major type and accounts for 80 to 90% of all instances of the disease. When a person suffers from psoriasis, red maculae or red papules having clear borders occur on portions of the patient's body which are susceptible to external phlogogenic stimuli, such as the head, elbows, knees and buttocks, and on areas where bacteria and fungi are likely to proliferate, such as pilose regions.

Various studies have heretofore been made on psoriasis, including conventional studies directed to the characterization of the morphological changes at the lesion site and more recent studies directed to the characterization of the bio-chemical and immunological changes at the lesion site. Nevertheless, the essential cause of psoriasis and the mechanism of occurrence of psoriatic lesions have not yet been elucidated. With respect to all types of psoriasis, various symptoms and phenomena are observed, such as hyperplasia and abnormal cornification of epidermal cells ascribed to the excess turnover of the cells by hypermetabolism; asthenia of inflammatory response in the epidermal papillary layer; vasodilation and serpiginous veins in the true skin; and polynuclear leukocyte migration and infiltration into epidermal cell layers.

Representative of the therapeutic methods heretofore available to physicians seeking to treat psoriasis are the control of the hyperfunctional proliferation of epidermal cells; control of the inflammatory response; promotion of immunomodulation; and avoidance of infection by bacteria and fungi. For example, the following therapeutic methods have conventionally been utilized:

(1) External and Internal Use of Adrenocortical Hormone

The external or topical use of a steroid, such as adrenocortical hormone, has the immediate effect of reducing the symptoms of psoriasis, particularly the reduction of eruptions. However, administration of adrenocortical hormone over long periods of time that are necessary in such treatment causes tachyphylaxis so that the dose must be increased, or stronger drugs must be used in order to attain a desired therapeutic effect. Occasionally, the occurrence of a new lesion is observed at a site which has been treated with the drug. When the adrenocortical hormone is applied to skin in the form of a coating, ointment, salve or paint, the hormone exerts its action not only on the lesion but also on the peripheral normal skin, so that atrophy and achromasia of true skin, or steroid acne, is disadvantageously caused to occur on such areas of the skin.

Further, when the administration of the hormone is interrupted in order to avoid adverse effects of the drugs, withdrawal dermatitis is often caused so that the lesion is likely to expand and deteriorate. Such withdrawal dermatitis is caused particularly when the administration of an internal preparation is discontinued. Accordingly, when the lesion occurs on a relatively large area of skin, the disease cannot be completely cured by this method alone and, therefore, this mode of therapy must be combined with other therapies.

(2) Photochemotherapy

This method consists of administering psoralen in the form of an external or internal preparation and applying longwave ultraviolet rays to the diseased part. However, several types of psoriasis cannot be treated by this method. Moreover, it has the disadvantage in that when it is applied for a long period of time as in the case of heliotherapy, not only is a phenomenon similar to the ageing of skin likely to occur, but also a peculiar lentigo is likely to be formed.

(3) Phototherapy (UV Irradiation)

As in the case of heliotherapy, when ultraviolet irradiation is carried out for a long period of time, not only is accelerated ageing of the skin likely to occur, but also carcinogenesis may be induced.

(4) External Use of Coal Tar

Coal tar suppresses the growth of epidermal cells so that the lesion is diminished over a short period of time and a relatively long remission period may be achieved. However, occasionally, stimulant dermatitis and folliculitis (tar acne) may be caused.

(5) Administration of Methotrexate

Methotrexate is an antagonist against folic acid, which is active in inhibiting the growth of cells. The use of methotrexate is effective for treating pustular psoriasis. However, the administration of methotrexate for a long period of time causes adverse effects, such as disturbance of liver function and suppression of myeloproliferation.

(6) Administration of Retinoid

Retinoid is considered to have an immunomodulation effect, that is, it may control the abnormal cornification of epidermal cells and the hyperfunction of leukocyte migration. The internal administration of retinoid, such as etretinate, is particularly effective for treating pustular psoriasis and psoriatic erythroderma. However, retinoid often exhibits an adverse effect wherein the thickness of skin and visible mucous membrane become small. Further, abnormal levels of serum lipoprotein are occasionally observed. Moreover, the retinoid is teratogenic and likely to accumulate and remain inside the body for a long period of time and, therefore, the application of retinoid to a person capable of childbearing is to be avoided. For this reason, retinoid is usually applied only to patients who are beyond child-bearing age or who are suffering from intractable psoriasis.

As mentioned above, although the use of adrenocortical hormone exhibits an immediate effect of reducing symptoms of psoriasis to some extent, tachyphylaxis is likely to occur, making the continued administration of the drug difficult. Further, owing to the tachyphylaxis, the dose must be disadvantageously increased. In such a case, when the administration is stopped in order to halt or avoid adverse effects, the symptoms may often become more severe due to the onset of withdrawal dermatitis. Accordingly, it is difficult to treat psoriasis effectively by the use of adrenocortical hormone alone. With respect to the other therapeutic methods, such as the photochemotherapy and therapy using an epidermal cell growth inhibitor such as coal tar, anthralin, methotrexate and retinoid, when these methods are used in combination with adrenocortical hormone, a therapeutic effect may be attained to some extent, but the psoriasis cannot be truly healed. See, Roenigk, H. H., Jr. and Maibach, H. I., "Psoriasis" (Marcel Dekker Inc., New York, 1985).

Accordingly, it is an object of the present invention to provide a novel pharmaceutical composition effective for the treatment of psoriasis.

Another object of the present invention is to provide a pharmaceutical composition useful in the treatment of psoriasis which is substantially free of the drawbacks in currently known formulations.

Another object of the invention is to provide a novel therapeutic method effective for treating psoriasis.

Yet another object is to provide a method of treating psoriasis using the pharmaceutical composition of the present invention which does not suffer the drawbacks of methods currently known or in use.

These and other objects and features of the invention as well as the advantages thereof can be fully understood by reference to the following description and claims.

2. SUMMARY OF THE INVENTION

The foregoing objects are achieved according to the present invention by the inventors' discovery of a new type of pharmaceutical composition and method for its use in the treatment of psoriasis, which are free from the above-mentioned drawbacks inevitably accompanying the conventional therapeutic compositions and methods. More particularly, it has been found that when tumor necrosis factor or "TNF" is administered to patient suffering from psoriasis, who could not be cured by any of the conventional therapeutical compositions and methods, the symptoms of the disease are diminished from the entire body of the patient.

According to the present invention, a new pharmaceutical composition for the treatment of psoriasis is provided which comprises TNF and at least one pharmaceutically acceptable carrier, diluent or excipient. A new method for treating psoriasis is also provided which comprises administering an effective antipsoriasic amount of TNF to a patient having psoriasis.

In the pharmaceutical compositions used for treating human psoriasis patients according to the invention, the tumor necrosis factor is preferably produced from a human-derived cell or by recombinant DNA technique. Such compositions can be adapted, e.g., for intravenous, intramuscular, subcutaneous, or intradermal injection, oral or rectal administration, external or topical application, or instillation. The pharmaceutical composition can be further adapted for the administration of a polypeptide composition.

Tumor necrosis factor or TNF was discovered originally in mouse serum after intravenous injection of bacterial endotoxin into mice primed with viable *Mycobacterium bovis*, strain Bacillus Calmette-Guerin (BCG). See, *Proc. Nat. Acad. Sci. U.S.A.*, 72(9), 3666–70 (1975). TNF-containing serum from mice is cytotoxic or cytostatic to a number of mouse and human transformed cell lines, but less so to normal cells in vitro. It causes necrosis of transplantable tumors in mice. TNF also occurs in the serum of rat, rabbit and guinea pig. Further, it is also known that TNF can be produced by mononuclear phagocytes, fibroblasts, B-cells, and the like derived from a mammal under certain conditions. In this connection, there are many reports in the literature which have been summarized by Lloyd J. Old in *Scientific American*, 258(5), 59–75 (May, 1988). In the present invention, the above-mentioned TNF obtained from serum or cells derived from a mammal can be used as an active ingredient. However, for purposes of utilizing the present invention on human patients, it is preferred to use pharmaceutical compositions containing human TNF from the standpoint of immunological compatibility.

Human TNF suitable for use in the present invention can be produced by recombinant DNA techniques. Alternatively, human TNF can also be produced by culturing cells derived from humans.

Suitable methods for producing human TNF by recombinant DNA techniques are described, for example, in Shirai T. et al., Nature, 313, 803–6 (1985) and Japanese Patent Application Laid-Open Specification No. 60-252496 (corresponds to European Patent Application Publication No. 0 158 286). By way of illustration, human TNF can be obtained by culturing E. coli to homogeneity. The activity of human TNF during purification is monitored by mouse L-cell killing activity using a modification of the method of Williamson et al. employing L-M cells (American Type Culture Collection, CCL 1.2). See, Moss B., Proc. Nat. Acad. Sci. U.S.A., 80, 5397–401 (1983). The number of surviving cells is determined by the photometric method of Ruff and Gifford, published in J. Immun., 125, 1671–7 (1980).

More particularly, human TNF can be produced as follows. Cells from a culture of E. coli K12 (D1212)/pHNtac4 in Luria broth containing 50 $\mu$g ml$^{-1}$ ampicillin are collected by centrifugation and passed 10 times through a Manton-Gaulin press (manufactured and sold by Gaulin Corp., U.S.A.). The supernatant cell lysate has a specific activity of 32,000 U mg$^{-1}$ of protein. The cell lysate is loaded onto a DEAE-Sepharose CL-6B (manufactured and sold by Pharmacia Fine Chemicals AB, Sweden) column equilibrated with 20 mM Tris-HCl (pH 8.0) and eluted at pH 8.0 with 20 mM Tris-HCl containing 100 mM NaCl. Fractions with L-cell killing activity are pooled and further concentrated in a polysulfone hollow fiber (manufactured and sold by Asahi Chemical Industry Co., Japan) with a molecular weight exclusion limit of 6,000. The concentrate is heated at 60° C. for 30 minutes with gentle stirring followed by filtration through an 0.2 $\mu$m membrane (manufactured and sold by Flow Laboratory, USA). The sample is loaded onto another DEAE-Sepharose CL-6B column (2.6×11 cm) equilibrated with 20 mM Tris-HCl(pH 8.0) containing 150 mM NaCl. The active material is eluted with 20 mM Tris-HCl(pH 8.0) containing 150 mM NaCl and the active fractions are pooled and loaded onto a Sephacryl S-200 column (manufactured and sold by Pharmacia Fine Chemicals AB, Sweden) in 5 mM sodium phosphate(pH 7.4) containing 150 mM NaCl. The active fractions correspond to the molecular weight of 45,000, with 41% recovery of TNF activity.

The thus-obtained human TNF has a specific activity of about $1.4 \times 10^6$ units/mg-protein and induces hemorrhagic necrosis of Meth A sarcoma transplanted in the peritoneal cavity of a BALB/c mouse. This TNF is still not completely purified. Accordingly, if desired, it can be purified further using the above-mentioned techniques alone or in combination in order to obtain human TNF having a higher degree of purity. The human TNF can also be produced by other known methods, including these described in Diane Pennica et al., Nature, 312, 20–7 (December, 1984); EP-A-168214; EP-A-155549; and the like.

The number of amino acids constituting human TNF varies depending upon the production method used to obtain the TNF. For example, human TNF produced by recombinant DNA techniques described in EP-A-0158286 consists of 155 amino acids, whereas human TNF produced by the method of Pennica et al., supra, consists of 157 amino acids, having an amino acid sequence composed of a sequence of the above-mentioned 155 amino acids and, attached to its N-terminus, 2 amino acids.

The human TNF produced by recombinant DNA technique also includes a polypeptide having a methionine moiety attached to the N-terminus of the above-mentioned amino acid sequence and an intermediate having a partial or entire signal peptide for human TNF attached to the N-terminus of the above-mentioned amino acid sequence. It is possible to change a portion of the structure of a DNA coding for a polypeptide by natural or artificial mutation without significant change in the activity of the polypeptide.

The human TNF which can be used in the present invention includes a polypeptide having a structure corresponding to homologous variant(s) of the polypeptide having the above-mentioned amino acid sequence. Examples of homologous variants include polypeptides described in U.S. Pat. Nos. 4,677,063 and 4,677,064, the disclosures in which are incorporated herein by reference. All such physiologically active polypeptides are also hereinafter referred to as "human TNF".

Natural human TNF is likely to undergo biochemical modification or chemical modification, and also likely to aggregate to form a multimer, such as a dimer or a trimer. These TNF polypeptides produced in nature are also hereinafter referred to as "human TNF", and can be used as an active ingredient in the pharmaceutical compositions of the present invention.

Further, lymphotoxin can be similarly used as an active ingredient in the pharmaceutical compositions of this invention.

The pharmaceutical compositions of the present invention can be formulated into various preparations adapted, for example, to intravenous, intramuscular, subcutaneous, and intradermal injection, oral or rectal administration, external application and instillation. It is advantageous that the preparations are adapted for the administration of a polypeptide composition.

In preparing the pharmaceutical compositions of the present invention, various additives can be included as may be appropriate, such as one or more carriers, diluents, excipients, fluidizing agents, binding agents, stabilizers, thickeners, pH adjusting agents and the like.

Suitable carriers, diluents and excipients include starches and derivatives thereof, such as potato starch, corn starch, dextrin and wheat starch and hydroxypropyl starch; sugars, such as lactose, glucose, sucrose, mannitol and sorbitol; celluloses, such as methylcellulose, carboxylmethylcellulose and hydroxypropylcellulose; inorganic compounds, such as sodium chloride, boric acid, calcium sulfate, calcium phosphate and precipitated calcium carbonate; and the like.

Suitable fluidizing agents include magnesium oxide, synthetic aluminum silicate, metasilicic acid, magnesium aluminum oxide, hydrous silicic acid, anhydrous silicic acid, talc, magnesium stearate, kaolin and the like.

Suitable binding agents include polyethylene glycol, polyvinyl pyrrolidine, polyvinyl alcohol, gum arabic, tragacanth, sodium alginate, gelatin, gluten, and the like.

Suitable stabilizers include proteins, such as albumin, protamine, gelatin and globulin; amino acids and salts thereof, and the like.

Suitable thickeners include sucrose, glycerin, methylcellulose, carboxymethylcellulose, and the like.

Suitable pH adjusting agents include hydrochloric acid, sodium hydroxide, phosphates, citrates, carbonates, and the like.

In cases where the pharmaceutical composition of the present invention is in the form of a tablet, a carrier such as starch, lactose or the like can be incorporated, in addition to the above-mentioned stabilizer.

The pharmaceutical compositions of the present invention can also be applied in the form of a paint, an ointment, a cream, or in any other forms of preparations adapted for topical application so as to facilitate infiltration of the active ingredient into the skin, such as an aerosol, a fomentation, a cataplasm and the like. In such a case, a surfactant, a tackifier, an oleaginous base and the like can be incorporated.

Suitable surfactants include sodium lauryl sulfate, Tween type surfactants (polyoxethyleneglycolsorbitan alkyl esters), Span type surfactants (acylsorbitan), and the like.

Suitable tackifiers include natural rubber, butyl rubber, polyisobutylene, polyalkylacrylate, polyterpene resins and the like.

Suitable oleaginous bases include higher aliphatic alcohols, higher fatty esters, waxes, triglycerides, monoglycerides, liquid paraffins, Isopar (coparaffinate), Vaseline® petroleum jelly (petrolatum), silicone oil, natural oils such as lanolin, improved vegetable oils and castor oil, and the like.

In another aspect, the present invention provides a method for treating psoriasis comprising administering an effective anti-psoriasic amount of tumor necrosis factor to a patient suffering from psoriasis.

The pharmaceutical compositions of the present invention can be administered to a psoriasis patient in an amount such that the daily dose of TNF for an adult is generally in the range of from about 50 to 100,000,000 units, and preferably from about 50 to 500,000 units in the case of local administration, from about 1,000 to 10,000,000 units in the case of general injection such as intravenous injection and intramuscular injection, and from about 10,000 to 100,000,000 units in the case of oral administration. The daily dose can be increased or decreased according to the patient's symptoms.

The term "unit" as used above means a quantity of TNF by which 50% of $1 \times 10^5$ cells/ml of L-M cells (American Type Culture Collection CCL 1.2) are killed. This quantity is measured as follows: As culture vessels, there are employed 96-well microtiter plates produced by Flow Laboratories, Inc. (U.S.A.). L-M cells are cultured in Eagle's minimum essential medium containing 1 v/v % of fetal calf serum [the composition of this medium is described, for example, in Tissue Culture, edited by Junnosuke Nakai et al., Asakura Shoten, Japan (1967)]. A sample (0.1 ml), serially diluted with the medium, and the L-M cell suspension (0.1 ml, $1 \times 10^5$ cells/ml) are mixed into each well of the plates and the plates are incubated at 37° C. for 48 hours in air containing 5% carbon dioxide. At the end of the culture period, 20 μl of glutaraldehyde is added to fix the cells. After fixation, the plates are washed with distilled water and allowed to dry, and 0.05% methylene blue (0.1 ml) is added to stain the viable cells. The plates are thoroughly washed with distilled water to remove excess dye and allowed to dry. Hydrochloric acid (0.36N) is added to each well to extract the dye from stained cells. Absorbance of each well at 665 nm is measured with Titertek Multiskan produced by Flow Laboratories, Inc. (U.S.A.). The absorbance is proportional to the number of viable cells. The above-mentioned quantity of the physiologically active polypeptide of the present invention by which 50% of $1 \times 10^5$ cells/ml of L-M are killed is obtained by a plotting of the dilution versus the absorbance.

The dosage regimen for treating a psoriasis patient with the pharmaceutical composition of the present invention varies according to the age and symptoms of the patient. As mentioned above, the composition can generally be administered over several days to several weeks in a daily dose of 50 to $10^8$ units. The daily dose can be administered to a patient all at once or in several applications. The adminstration of the present pharmaceutical composition can be conducted each day, or alternatively, the administration can be conducted at intervals. Representative examples of the dosage regimen are as follows:

(a) daily administration for 1 to 4 weeks;

(b) daily administration for 1 to 6 days, alternately with a pause for one day to several weeks;

(c) administration for one day per week; and (d) daily administration for 5 days, alternately with a pause of one month.

The pharmaceutical compositions of the present invention are extremely effective for treating psoriasis. When the composition is administered to a patient who has suffered from psoriasis for a long time, the systemic symptoms of the disease are completely diminished within a short period of time.

3. DESCRIPTION OF PREFERRED EMBODIMENTS

The present invention is illustrated by the following non-limiting examples.

REFERENCE EXAMPLE

Human TNF composed of 155 amino acids is produced by means of recombinant DNA technique according to the method described in European Patent Application Publication No. 0,158,286, the disclosure in which is incorporated herein by reference.

The cytotoxic activity of the thus-obtained human TNF against human tumor cell lines is evaluated as follows:

One thousand cells are cultured on a 96-well microplate containing 0.2 ml/well of various concentrations of human TNF ($1 \times 10^4 - 6 \times 10^{-4}$ U/ml). After a 5–7 day incubation, control cells that have grown in a well containing no drug become confluent. The number of surviving cells is then measured by methylene-blue-uptake.

The results are shown in Table 1 below. Among the 26 human tumor cells lines, 4 (15.3%) are hypersensitive (+++: IC50≦1.0 U/ml), 6 (23.1%) are highly sensitive (++: IC50≦10,000 U/ml), 9 (34%) are sensitive (+: inhibition ratio≧20%) and 7 (20.9%) are non-sensitive (−: inhibition ratio<20%). Thus, 73% of the tumor cell lines are found to be sensitive to human TNF. In contrast, no cytotoxicity is observed against normal diploid cell lines, and growth stimulation is observed in some normal cell lines.

TABLE 1

| Origin | Cell line | Culture periods (Hrs) | Cytotoxic activity * | Maximum inhibition (%)** |
|---|---|---|---|---|
| Neuroblastoma | SYM-1 | 118 | ++ | 65 |
|  | NB-1 | 162 | + | 31 |
|  | GOTO | 144 | + | 25 |
| Oral cancer | KB | 119 | ++ | 80 |
| Lung cancer | PC-10 | 112 | +++ | 72 |
|  | SK-LU-1 | 168 | + | 48 |
|  | PC-8 | 168 | + | 35 |
| Breast cancer | BT-20 | 168 | +++ | 81 |
|  | MCF-7 | 168 | ++ | 79 |
| Stomach cancer | MKN-45 | 168 | ++ | 61 |
|  | KATO-3 | 168 | + | 40 |
|  | MKN-28 | 162 | + | 28 |
| Melanoma | HMV-1 | 114 | − | 9 |
|  | HMV-2 | 162 | − | 8 |
|  | SEKI | 114 | − | 0 |
| Osteosarcoma | SK-ES-1 | 161 | + | 37 |
|  | U-2-OS | 115 | + | 30 |
|  | SAOS-2 | 161 | − | 12 |
| Myosarcoma | KYM-1 | 168 | +++ | 100 |
| Monocytic leukemia | THP-1 | 168 | +++ | 100 |
| Wilm's tumor | W-2 | 168 | ++ | 94 |
| Colon cancer | SK-CO-1 | 168 | + | 24 |
| Bladder cancer | T-24 | 119 | − | 1 |
| Uterus cancer | SK-UT-1 | 141 | − | 13 |
| Cervix cancer | ME-180 | 119 | ++ | 74 |
|  | HELA | 119 | − | 0 |
| Normal diploid | HEL | 144 | − | 2 |
|  | HEK | 144 | − | 0 |
|  | HET | 166 | − | 0 |
|  | MRHF | 160 | − | 0 |

*+++: $IC_{50} \leq 1.0$ U/ml
++: $IC_{50} \leq 10,000$ U/ml
+: Inhibition ratio $\geq 20\%$
−: Inhibition ratio $< 20\%$
**Drug conc. $\leq 10,000$ U/ml Example 1

A 10-fold dilution of a serum obtained from a mouse infected with lactic dehydrogenase virus (LDV), and which has been stored at the Pharmaceutical Laboratory of Asahi Chemical Industry Co., Ltd., Japan is inoculated into the back of each of seven BALB/c nu/nu mice in an amount of 0.05 ml. Among the seven inoculated mice, five mice exhibit a pathological change, a knob. These mice each having the pathological change are used as a model of psoriasis.

Ten days after inoculation of the above-mentioned serum dilution, the size of the knob-like lesion of each mouse becomes about 3 to 10 mm in diameter. Human TNF obtained in the above Reference Example is intravenously injected into the mice in an amount of 1,000 to 3,000 units. Five (5) days after the injection, the lesion portions of the mice are examined visually. The results are shown in Table 2, below.

TABLE 2

| Mouse No. | Size of lesion (mm) (10 days after the serum injection) | Dose (unit) | Results (5 days after the TNF injection) |
|---|---|---|---|
| 1 | 3 × 5 | 0 | Not changed |
| 2 | 5 × 8 | 1000 | Yellow scab is formed on the lesion portion |
| 3 | 5 × 5 | 1000 | Color of the lesion portion is changed to dark red |
| 4 | 3 × 3 | 3000 | Color of the lesion portion is changed to dark red |
| 5 | 10 × 8 | 3000 | Necrosis occurs and the lesion portion comes off |

The results shown in Table 2 confirm the therapeutic activity of TNF against psoriasis.

Example 2

Human TNF is produced by recombinant DNA technique according to the above Reference Example. Using the thusproduced recombinant human TNF, a lyophilized preparation for injection having the following composition is formulated:

| Formulation | |
|---|---|
| Human TNF | $5 \times 10^5$ units |
| D-Mannitol | 30 mg |
| Normal serum albumin (human) | 10 mg |
| Sodium chloride | 2.0 mg |
| Sodium dihydrogen phosphate dihydrate (adjusted at pH6.8 by sodium hydroxide) | 3.9 mg |

Example 3

The lyophilized preparation prepared in Example 2 is dissolved in 2 ml physiological saline and the resultant solution is diluted with physiological saline to a final volume of 100 ml.

The resultant dilute solution is administered to a 70-year-old female patient by intravenous infusion over one hour at a dosage of $4.5 \times 10^5$ units per m² of body surface area of the patient. The administration is conducted daily for 5 days. The course is repeated after a three-week rest period.

The patient had suffered from psoriasis for 25 years. She has taken various OTC (over-the-counter) drugs to treat her condition, but to no therapeutic effect. Thereafter, the use of such OTC drugs was discontinued for 2 years. However, 3 weeks after completion of the above-mentioned treatment with human TNF, all of the symptoms have disappeared and the patient is deemed completely healed.

We claim:

1. A method for treating noncontagious psoriasis, comprising intraveneously administering a pharmaceutical composition, consisting essentially of an effective anti-psoriatic amount of tumor necrosis factor and at least one pharmaceutically acceptable carrier or diluent, to a patient having psoriasis.

2. The method according to claim 1, wherein said tumor necrosis factor is produced from a human derived cell.

3. The method according to claim 1, wherein said tumor necrosis factor is produced by means of recombinant DNA technique.

* * * * *